United States Patent [19]

Mangum

[11] Patent Number: 5,397,326
[45] Date of Patent: Mar. 14, 1995

[54] KNOT PUSHER FOR VIDEOENDOSCOPIC SURGERY

[76] Inventor: William K. Mangum, 2020 16th St., Greeley, Colo. 80631

[21] Appl. No.: 47,852

[22] Filed: Apr. 15, 1993

[51] Int. Cl.$^6$ ............................................. A61B 17/00
[52] U.S. Cl. ................... 606/148; 606/139; 289/17
[58] Field of Search ................ 606/1, 103, 139, 144, 606/148, 207; 289/17

[56] References Cited

U.S. PATENT DOCUMENTS

| | | | |
|---|---|---|---|
| 671,337 | 4/1901 | Gibson | 606/148 |
| 2,131,321 | 9/1938 | Hart | 606/139 |
| 2,595,086 | 4/1952 | Larzelere | 606/139 |
| 4,819,640 | 4/1989 | Narayanan et al. | 606/148 |
| 5,176,691 | 1/1993 | Pierce | 606/148 |
| 5,192,287 | 3/1993 | Fournier et al. | 606/139 |
| 5,201,744 | 4/1993 | Jones | 606/148 |
| 5,234,444 | 8/1993 | Christoudias | 606/139 |
| 5,257,637 | 11/1993 | El Gazayerli | 606/148 |
| 5,269,791 | 12/1993 | Mayzels et al. | 606/148 |

FOREIGN PATENT DOCUMENTS 0305885 6/1971 U.S.S.R. ................ 606/139

Primary Examiner—Stephen C. Pellegrino
Assistant Examiner—Jeffrey A. Schmidt
Attorney, Agent, or Firm—David S. Woronoff

[57] ABSTRACT

Four embodiments of videoendoscopic knot pushers are shown having a main body and first and second fingers whose ends are shaped in a smooth rounded shape to guide a suture and knot into position with a patient's body. The finger members define either a "V" shaped cleft or a smooth walled channel between them for grasping the suture. One embodiment of the invention has second and third channels for retaining the suture in the fingers even during retraction of the main body. Another embodiment of the present invention has a spiral channel formed "upstream" of the finger members for retaining control of the suture even if the suture slips out of the grasp of the channel formed by the first and second finger members.

6 Claims, 4 Drawing Sheets

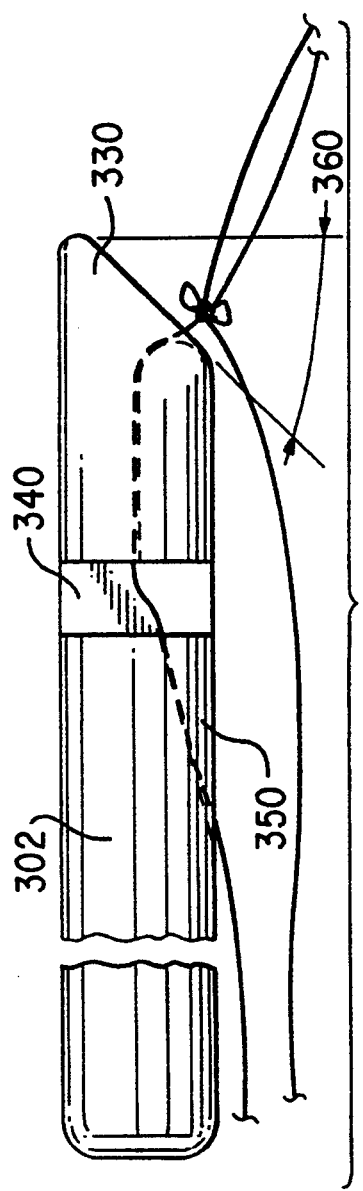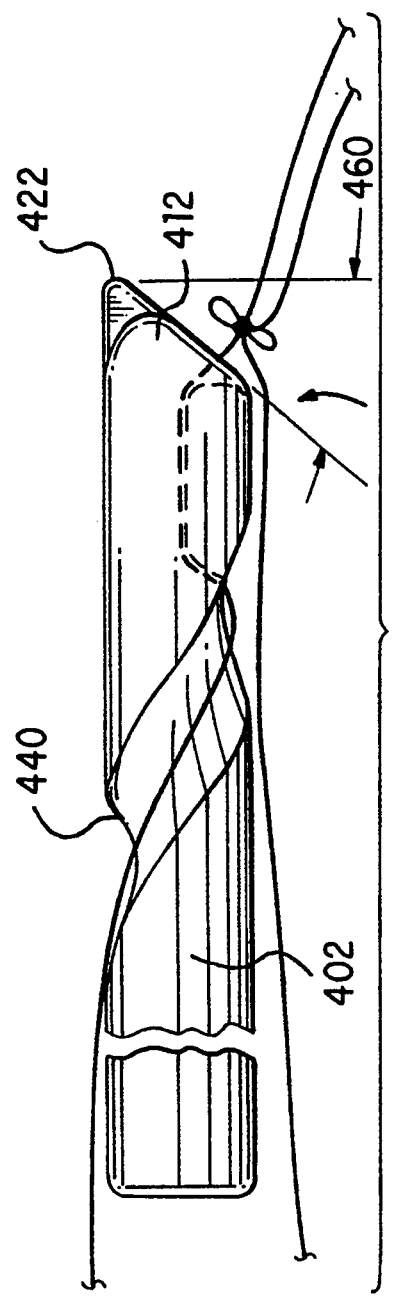

KNOT PUSHER FOR VIDEOENDOSCOPIC SURGERY

BACKGROUND OF THE INVENTION

The present invention relates to a number of novel embodiments of a knot pusher for use in videoendoscopic surgery. The key element of the embodiments is structure for retaining a positive grip on the knots to be pushed through the sheath, which remains after removal of the trochar, and into the body of the patient receiving the surgical procedure.

FIELD OF THE INVENTION

The present invention relates to the field of knot pushers used in videoendoscopic surgery. Videoendoscopic surgery is surgery performed through a number of small openings formed in the patient's body by a small tube (trochar) with surgical blades on the end. Initially, for either abdominal or chest surgery, an incision is made in the skin and the bladed end of a trochar, which has a sheath on its outside, is inserted into to the body to form one of the working incisions. The incisions made are quite small, usually, of the order of between 5 and 12 mm. The entire surgical procedure is performed by instruments inserted through the trochar's sheath and into the patient's body including the cutting, sewing, cauterizing and removal of any tissue, fluids, etc. If the surgery is intra-abdominal, distention of the cavity is obtained by pumping carbon dioxide into the cavity to inflate it slightly in order to give the surgeons space in which to work. To maintain this pressure, all devices inserted through the trochar's sheath must be sealed. For this purpose, such sheaths have valves formed on them to close around the instruments inserted through them.

In order for the surgeon to observe the work area and his instruments, some sheaths must have light brought through them into the body and a camera image brought out. The operating surgeon and his team watch the surgery on a two dimensional screen, usually a video screen. The conventional larger field surgery uses the three dimensional image that is obtained by opening the patient up with a large incision. The advantages to the patient of the videoendoscopic techniques are well known.

Most surgical procedures require the tying of knots to close incisions, to repair torn tissues, to re-attach tissue, to stop bleeding, etc. In videoendoscopic surgery, the knots can be tied either inside the body or tied outside of the body and pushed through the sheath to the site to be tied. Because it is far simpler for the surgeon to work outside of the body than inside, the surgeon will prefer to tie the surgical knot outside of the body and push it through the sheath to the proper site. Learning the techniques and skills to tie surgical knots inside the body (intra-corporeal) is time consuming and difficult. Further intra-corporeal knot tying exposes the patient to some additional risk of injury from a misdirected needle. The tool that pushes the surgical knot through the sheath is known as a "knot pusher". The present invention relates to knot pushers for use in videoendoscopic surgery. The knot pushers are formed of a relatively rigid, sterilizable material.

DESCRIPTION OF THE PRIOR ART

The closest prior art known to the applicant are devices which are commercially available and are known as the Clarke-Reich Ligator which is manufactured for two sizes "micro" and "macro" for handling sutures in sizes 6-0 and smaller or 5-0 and larger, respectively. The Clarke Ligator, Reddick-Saye Style for 5-0 and larger sutures is also believed to be art prior to the invention described herein.

There is also art known to the inventor known as the "heliX" knot pusher which has been shown in a publication entitled General Surgery and Videoendoscopic News, Volume 14, published in March, 1993. This device, a variation of the basic Clark-Reich Ligator with a helix formed on its lower end, is not prior art to the present invention.

The prior art Clarke and Clarke-Reich ligators show cylinders having an essentially circular shaped aperture extending from one end in which the circle has a gap formed in the circumference to admit the suture and to hold the knot at the base of the ligator.

SUMMARY OF THE INVENTION

The present invention teaches four novel embodiments of a knot pusher for use in suturing in videoendoscopic surgery. Each of the embodiments discloses a novel structure for keeping control of the knot as the knot is propelled through the sheath into the patient's body and onto the place where the suture is to be secure. Each embodiment is an improvement over the known knot pushers because the knot being pushed is positively retained in control by the knot pusher.

The embodiment of the invention shown in FIG. 3 is adapted to entrap the suture and knot in its upper and lower slots during the entire travel through the sheath to the place where the knot is to be drawn tight.

The embodiment of the invention shown in FIG. 4 is adapted to engage the suture in the slot formed in its end and to further engage the upper portion of the suture in the spiral grove which extends about 270° around the periphery of the knot pusher. In this embodiment of the present invention, if the suture slips out of the slot, rotation of the knot pusher will enable that portion of the suture engaged by the spiral groove to guide the suture into position back in the slot.

Each embodiment of the present invention keeps the suture and knot under more positive control than the known prior art. In particular, each embodiment of the present invention is believed to be unique in its ability to push and secure the slipknots used in videoendoscopic surgery. In part this unique ability arises from the small size of the slot relative to the size of the suture. In FIGS. 3 and 4, the slots are one-sixty-fourth inch wide and one-eighth inch deep for sutures from 3-0 to 0. In FIGS. 1 and 2 the notch at the base of the "V" cleft is also about one-sixty-fourth inch wide.

During videoendoscopic surgery using the prior art devices there was the relatively frequent loss of the suture either in the sheath or within the patient's body. In either case, the surgeon would have to regain control of the suture and knot and attempt to replace the knot properly. Loss of the knots contributed to extension of the time for surgery and therefore to extension of time for the patient to be anesthetized and to a possible extension of time for the patient to lose blood or some other vital fluid. These events are unpleasant at best and dangerous at worst. The present inventive knot pushers by preventing or greatly reducing the occurrence of such events contribute to improved surgery and improved patient care.

BRIEF DESCRIPTION OF THE DRAWINGS

FIGS. 7, 8, 9, and 10 show the four embodiments of the present invention engaging sutures and knots. FIGS. 7, 8, 9, and 10 relate respectively to FIGS. 1, 2, 3 and 4 of the invention.

DESCRIPTION OF THE PREFERRED EMBODIMENT

Figure 1:
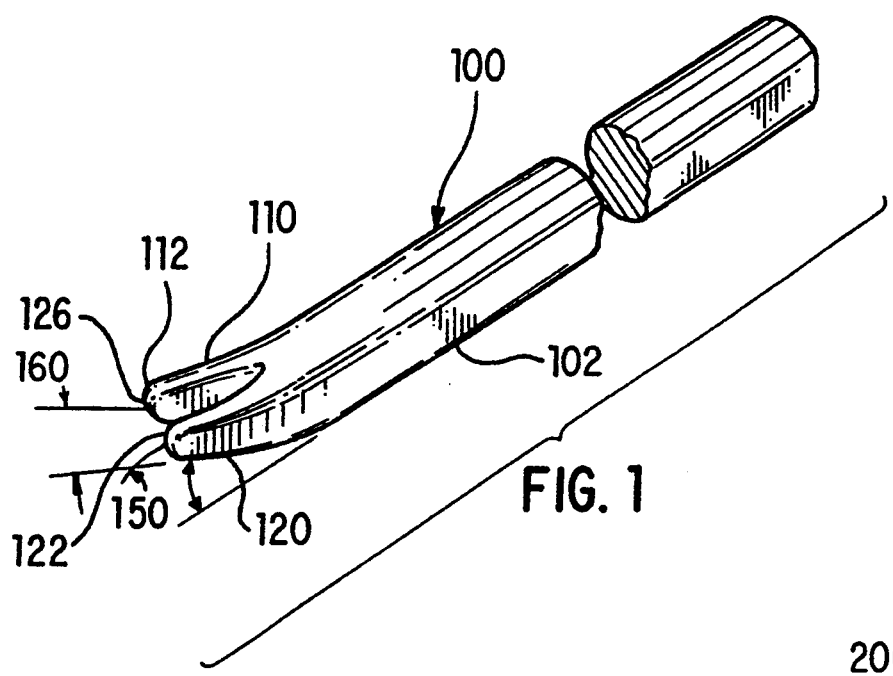
FIG. 1 shows a front perspective view of one embodiment 100 of the present invention.

FIG. 1 is a perspective view of the first embodiment of the present invention showing the present invention generally by the number 100. Knot pusher 100 has a main body 102 (about twelve inches long and about three-sixteenths of an inch in diameter) formed at one end into first and second finger members, 110, 120. The first and second finger members have respective ends 112, 122. A "V" shaped cleft 126 is formed between the finger members which has an opening of about one-sixteenths of an inch at its widest part. The finger members are tapered to be of reduced thickness near the rounded end. An acute angle 160 is formed between the finger members themselves and another acute angle 150 is formed between the finger members and the main body 102.

Figure 2:
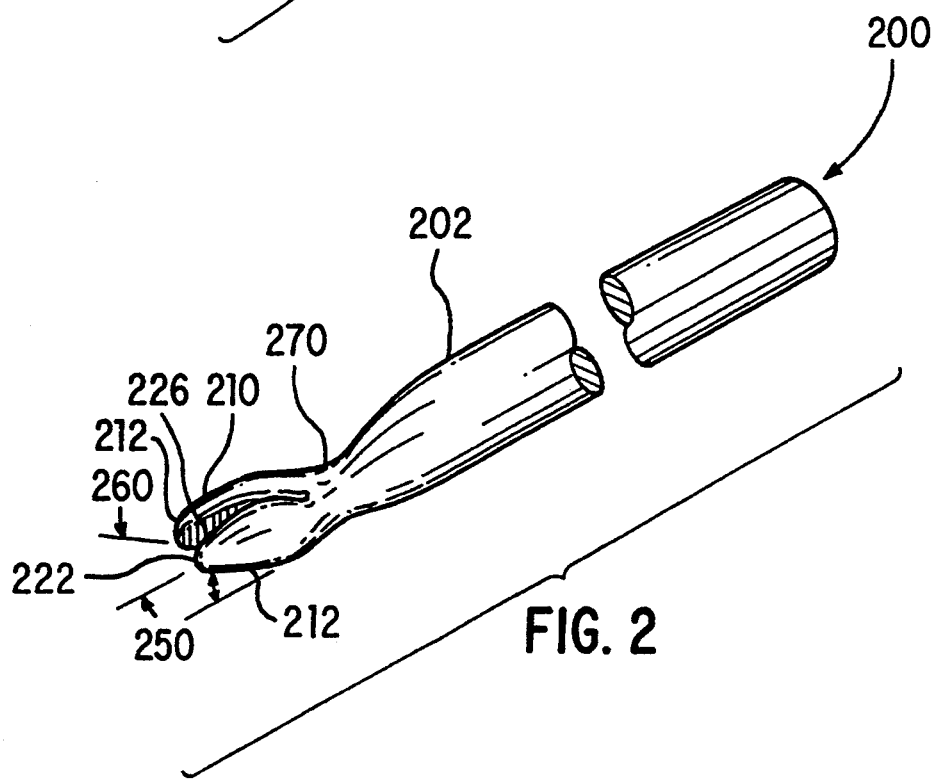
FIG. 2 shows a front perspective of a second embodiment 200 of the present invention.

FIG. 2 is a perspective view of the second embodiment of the present invention showing the present invention generally by the number 200. Knot pusher 200 has a main body 202 (about twelve inches long and about three-sixteenths of an inch in diameter) formed at one end into first and second finger members, 210, 220. The first and second finger members have respective ends 212, 222. A "V" shaped cleft 226 is formed between the finger members which has an opening of about one-sixteenths of an inch at its widest part. The finger members are tapered to be of reduced thickness near the rounded end. An acute angle 260 is formed between the finger members themselves and another acute angle 250 is formed between the finger members, 210,220 and the main body 202. A rigid elbow 270 is formed in the main body 202 near the beginning of the outwardly extending finger members.

Figure 3:
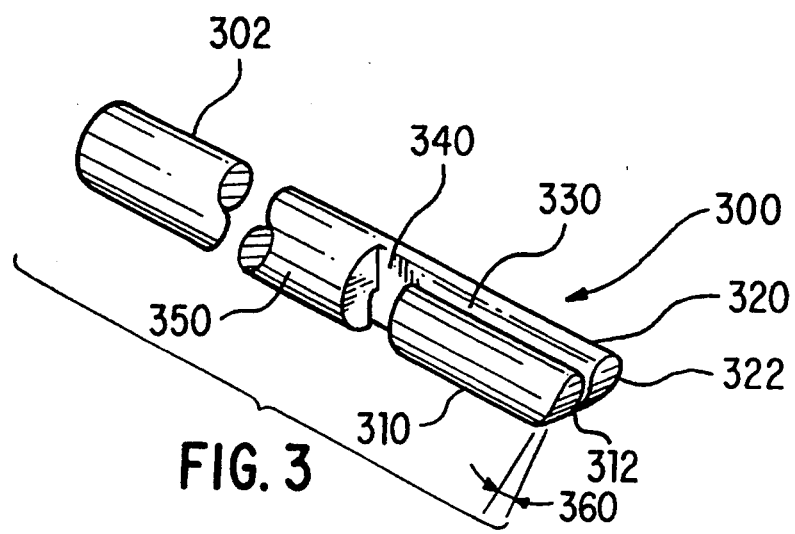
FIG. 3 shows a front perspective of a second embodiment 300 of the present invention.

FIG. 3 is a perspective view of the third embodiment of the present invention showing the present invention generally by the number 300. Knot pusher 300 has a main body 302 (about twelve inches long and about three-sixteenths of an inch in diameter) formed at one end into first and second finger members, 310, 320. The first and second finger members have respective ends 312, 322. A "U" shaped channel 330 is formed between the finger members Which has an opening of about one-sixty-fourth of an inch wide and about one-eighth inch deep. The finger members are tapered to a rounded end which forms an angle 360 with the main body 302. A second channel 340 is formed transverse to the first channel 330 and runs from the outer edge of the main body to the more remote side of the first channel 330. A third "U" shaped channel 350 is formed in the under side (as shown in the drawing) of the main body and runs longitudinally along the main body away from the first channel 330. The first and third channels, 330, 350 are interconnected by the second channel 340.

Figure 4:
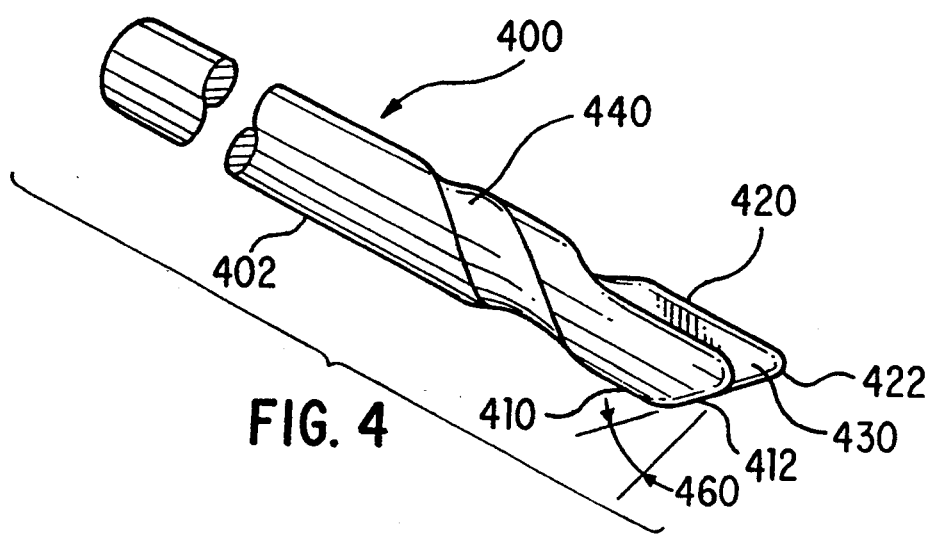
FIG. 4 shows a front perspective of a second embodiment 400 of the present invention.
Figure 5:
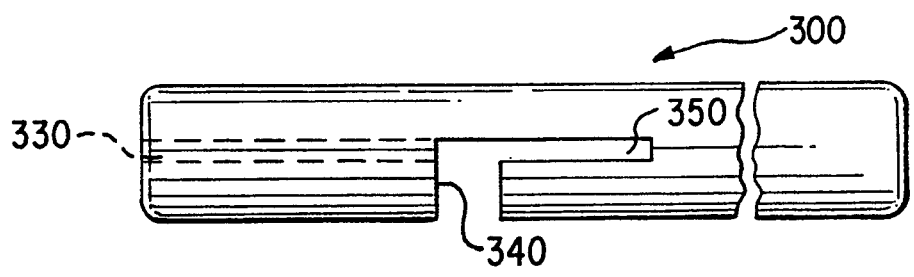
FIGS. 5 and 6 show a bottom view of the embodiments of the invention shown in FIGS. 3 and 4 respectively.
Figure 6:
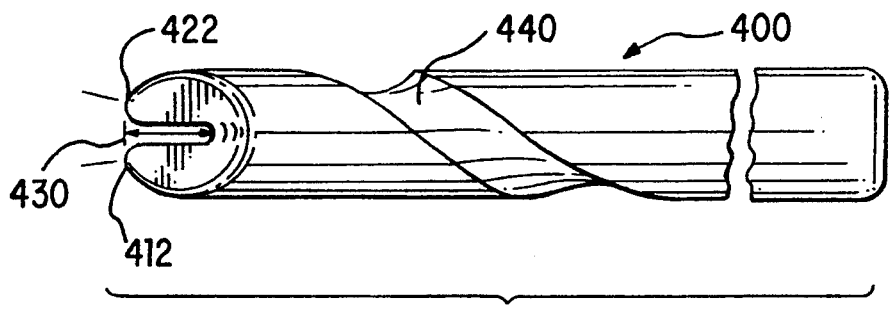
Figure 7:
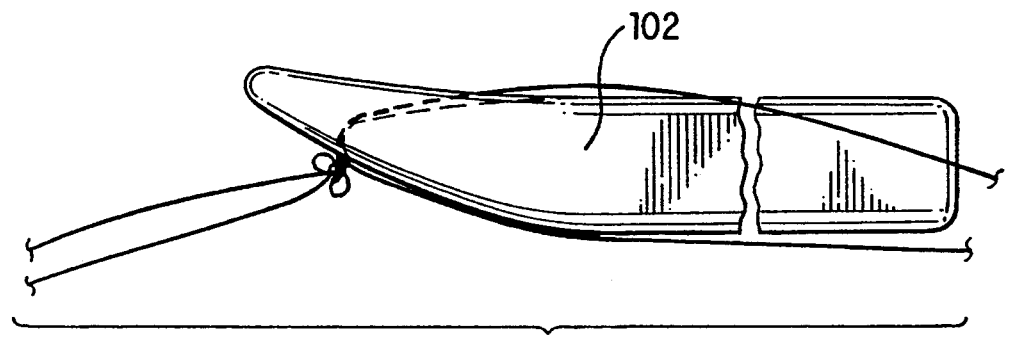
Figure 8:
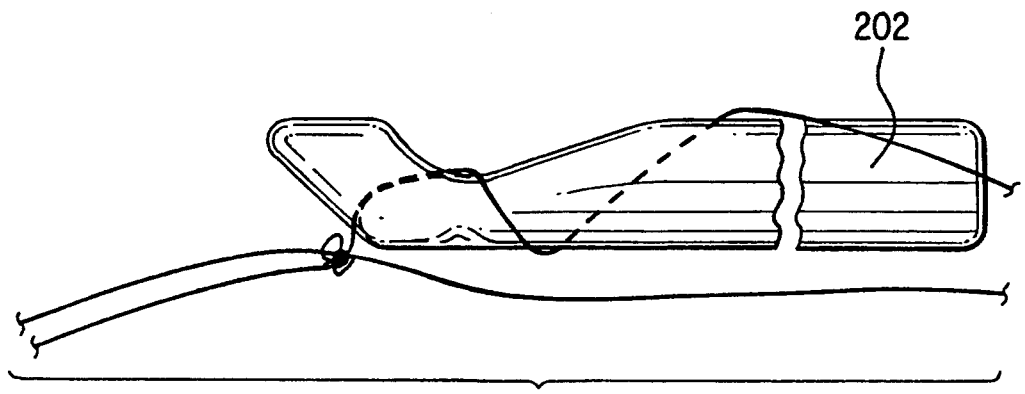

FIG. 4 is a perspective view of the fourth embodiment of the present invention showing the present invention generally by the number 400. Knot pusher 400 has a main body 402 (about twelve inches long and about three-sixteenths of an inch in diameter) formed at one end into first and second finger members, 410, 420. The first and second finger members have respective ends 412, 422. The end 422 of the knot pusher is slightly longer and higher than the end 412. A "U" shaped channel 430 is formed between the finger members which has an opening of about one-sixtyfourth of an inch wide and about one-eighth inch deep. The finger members are tapered to a rounded end which forms an angle 460 with the main body 402. A second spiral channel 440 is formed transverse to the first channel 430 and runs from the outer and upper edge of the first channel for about one inch along the length of the main body 402.

Important aspects of the techniques of videoendoscopic surgery are shown in a teaching video tape entitled *Video Perspective in Surgical Laparoscopy, Videoendoscopic Suturing and Knot-tying Techniques*, published in 1993 by Quality Medical Publishing, Inc.

In use each embodiment of the present invention provides an advanced implement from what is shown in the video tape described above. The suture to be inserted in the patient's body is in the form of a loop with a slip knot formed on one side. The first and second embodiment of knot pushers (the devices shown in FIGS. 1 and 2) engage the free ends of the sutures in the "V" cleft formed between the first and second fingers. The knot is engaged by the rounded lower surface of the knot pusher below the cleft. The FIG. 2 embodiment which has the elbow 270 is somewhat better able to retain the knot in position in the "V" cleft. In use, the second embodiment knot pusher is rotated one complete revolution after engaging the knot to hold the suture while the knot is being pushed through the sheath.

The FIG. 3 embodiment of the invention locks the suture in the first and third channels of the knot pusher. The angled end of the knot pusher aids in locking the suture in the channels.

The FIG. 4 embodiment engages the suture and knot as shown in FIG. 10. The suture is in the slot, and with rotation of the knot pusher two revolutions, in the spiral groove. The end 422 of the knot pusher is slightly longer and higher than the end 412. If the suture slips out of the slot 430, the end 422 will direct the suture back into slot 430 by drawing back slightly on the knot pusher 402 and allowing the suture wrapped on the spiral to slip over the smaller end 412.

The present invention has been shown and described with reference to four specific embodiments. The dimensions of the embodiments are given merely to gain an understanding of the scale of the inventions and the relative relationships between the size of the sutures employed and the size of the slots in the embodiments described in FIGS. 3 and 4 and the "V" shaped cleft described in FIGS. 1 and 2. These embodiments are illustrative of the main principles of the invention but the following claims shall not be limited to the embodiments shown. The claims are intended to cover and do cover those variations of the invention which are apparent to those skilled in the art.

I claim:

1. A knot pusher for use in videoendoscopic surgery comprising:
    a main body member formed of a rigid material suitable for sterilization having a distal end and a proximal end;
    the main body member having a continuous and smooth outer surface for main with a soft flexible seal;
    the distal end of the main body member formed into first and second outwardly extending finger members;
    the first and second finger members each have rounded and tapered ends formed thereon;
    a first "U" shaped slot is formed on an upper surface of the main body member;
    a second "U" shaped slot is formed in the bottom of the main body member;
    a third slot is formed transversely from the upper surface to the bottom of the main body member to interconnect the first and second "U" shaped slot members.

2. A knot pusher for use in videoendoscopic surgery comprising:
    a main body member formed of a rigid material suitable for sterilization having a distal end and a proximal end;
    the main body member having a continuous and smooth outer surface for mating with a soft flexible seal;
    the distal end of the main body member formed into first and second outwardly extending finger members;
    the first and second finger members each have rounded ends formed thereon:
    a spiral groove is formed in the outer surface of the main body member;
    the spiral groove communicates with the first and second finger members.

3. A knot pusher for use in videoendoscopic surgery comprising:
    a main body member formed of a rigid material suitable for sterilization having a distal end and a proximal end;
    one end of the main body member formed into first and second outwardly extending finger members;
    the first and second finger members each have rounded and tapered ends formed thereon;
    a first "U" shaped slot is formed between the first and second finger members;
    a spiral groove is formed in the outer surface of the main body member in a right hand direction of rotation;
    the spiral groove communicates at one end with the first "U" shaped slot member.

4. The knot pusher claimed in claim 3 for pushing knots formed in surgical suture material which has a diameter wherein:
    the "U" shaped slot member has a width only slightly larger than the diameter of the suture material.

5. The knot pusher claimed in claim 3 for pushing knots formed in surgical suture material which has a diameter wherein:
    the "U" shaped channel has a width only slightly larger than the diameter of the suture material.

6. A knot pusher for use in videoendoscopic surgery comprising:
    a main body member formed of a rigid material suitable for sterilization having a distal end and a proximal end;
    the main body member having a continuous and smooth outer surface for mating with a soft flexible seal;
    the distal end of the main body member formed into first and second outwardly extending finger members;
    the first and second finger members each have rounded and tapered ends formed thereon;
    a spiral groove is formed in the outer surface of the main body member;
    the spiral groove communicates with the first and second finger members.

* * * * *